United States Patent
Kawanishi

(10) Patent No.: US 10,130,321 B2
(45) Date of Patent: Nov. 20, 2018

(54) CONTROL APPARATUS, CONTROL METHOD, AND PROGRAM

(71) Applicant: CANON KABUSHIKI KAISHA, Tokyo (JP)

(72) Inventor: Tomohiro Kawanishi, Tachikawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 50 days.

(21) Appl. No.: 15/046,798

(22) Filed: Feb. 18, 2016

(65) Prior Publication Data

US 2016/0249873 A1  Sep. 1, 2016

(30) Foreign Application Priority Data

Feb. 26, 2015 (JP) .................. 2015-037334

(51) Int. Cl.
| | | |
|---|---|---|
| *H05G 1/58* | (2006.01) | |
| *A61B 6/00* | (2006.01) | |
| *G16H 40/63* | (2018.01) | |
| *G06F 19/00* | (2018.01) | |

(52) U.S. Cl.
CPC ........... *A61B 6/465* (2013.01); *A61B 6/4283* (2013.01); *A61B 6/467* (2013.01); *A61B 6/547* (2013.01); *A61B 6/548* (2013.01); *G06F 19/00* (2013.01); *G16H 40/63* (2018.01)

(58) Field of Classification Search
CPC ............ A61B 6/00; A61B 6/465; A61B 6/467
USPC ....................................... 378/116
See application file for complete search history.

(56) References Cited

U.S. PATENT DOCUMENTS

2015/0131782 A1* 5/2015 Park .................. A61B 6/4283
378/62

FOREIGN PATENT DOCUMENTS

JP   2013-039198 A   2/2013

* cited by examiner

*Primary Examiner* — Jurie Yun
(74) *Attorney, Agent, or Firm* — Fitzpatrick, Cella, Harper & Scinto

(57) ABSTRACT

To provide a technique which can reduce a working load and a mistake of the operation when introducing a radiation detector, a control apparatus has: a display control unit for causing a display unit to display a selecting screen for presenting a list of registered radiation detectors and receiving a selection from the list; and an associating unit for associating in such a manner that when an unregistered radiation detector is registered, imaging information regarding a radiation imaging associated with the radiation detector selected through the selecting screen is associated with the unregistered radiation detector.

18 Claims, 13 Drawing Sheets

FIG. 3A

| Name | Detector Group | Position Type |
|---|---|---|
| Workspace_50G_01 | 50G | Stand |
| Workspace_50G_02 | 50G | Cassette |
| Workspace_70C | 70C | Cassette |
| Workspace_401G | 401G | Cassette |

Property — 305    [Add] 303   [Delete] 304

Name: Workspace_50G_01 ~306
Position Type: Stand ▼ ~307
Detector Group: 50G ▼ ~308
Color: Green ▼ ~309

Detector:  310

| | Model Name | Serial Number | Detector Group |
|---|---|---|---|
| ☑ | CXDI50G-B-32 | 10000000 | 50G |
| ☐ | CXDI55G-S-32 | 14000000 | 50G |
| ☐ | CXDI70C-Wireless-F2 | 1800FF01 | 70C |
| ☐ | CXDI401G | 1A00FF01 | 401G |

[OK] 311   [Cancel] 312

Name: Workspace01 ~314
Position Type: Stand ▼ ~315
Detector Group: 50G ▼ ~316
Color: Green ▼ ~317

Detector: 318

| | Model Name | Serial Number | Detector Group |
|---|---|---|---|
| ☐ | CXDI50G-B-32 | 10000000 | 50G |
| ☐ | CXDI55G-S-32 | 14000000 | 50G |
| ☐ | CXDI70C-Wireless-F2 | 1800FF01 | 70C |
| ☐ | CXDI401G | 1A00FF01 | 401G |

[OK] 319   [Cancel] 320

FIG. 6

| Please Specify Detector. | | | | |
|---|---|---|---|---|
| Detector : | | | | |
| | Model Name | Associate Workspace | Detector Group | Serial Number |
| ☑ | CXDI50G-B-32 | WS-50G, WS-55G | 50G | 10000000 |
| ☐ | CXDI55G-S-32 | WS-55G | 50G | 14000000 |
| ☐ | CXDI70C-Wireless-F2 | WS-70C | 70C | 1800FF01 |
| ☐ | CXDI401G | WS-401G | 401G | 1A00FF01 |
| ☐ | CXDI80C-Wireless | WS-80C | 80C | 1900FF01 |
| ☐ | CXDI701C-Wireless | WS-70C | 70C | 2300FF01 |
| ☐ | CXDI60G-S-32 | WS-60C | 60G | 13000000 |

[ OK ]  [ Cancel ]

FIG. 8

| | Name | Position Type | Detector Group | Color |
|---|---|---|---|---|
| ☐ | WS-50G | Stand | 50G | Green |
| ☑ | WS-50G | Table | 50G | Purple |
| ☐ | WS-70C | Table | 70C | Purple |
| ☐ | WS-401G | Cassette | 401G | Light Blue |
| ☐ | WS-80C | Universal | 80C | Purple |
| ☑ | WS-70C | Stand | 70C | Orange |
| ☐ | WS-70C | Table | 70C | Orange |

Please specify at least one Workspace.
Workspace:

[ OK ]   [ Cancel ]

FIG. 10

| SUBSTITUTABLE | NAME OF SUBSTITUTION-TARGET RADIATION DETECTOR | S/N OF SUBSTITUTION-TARGET RADIATION DETECTOR |
|---|---|---|
| True | CXDI-70C-Wireless-F2 | 1800FF01 |

FIG. 12A

| ASSOCIATED COMBINATION INFORMATION | NAME OF RADIATION DETECTOR | TYPE OF RADIATION DETECTOR |
|---|---|---|
| WS-70C-Stand WS-70C-Table | CXDI-70C-Wireless-F2 | 70C |

DO YOU USE AS SUBSTITUTE APPARATUS OF FOLLOWING RADIATION DETECTOR?

Detector Info: 1222

| Name | Associate Workspace | Detector Group |
|---|---|---|
| CXDI70C-Wireless-F2 | WS-70C-Stand WS-70C-Table | 70C |

Yes  No 1223  1224

CONTROL APPARATUS, CONTROL METHOD, AND PROGRAM

BACKGROUND OF THE INVENTION

Field of the Invention

The present invention relates to a control apparatus, a control method, and a program.

Description of the Related Art

Hitherto, in the imaging of a radiation image (particularly, X-ray image using an X-ray) in a medical field, a radiation imaging system for imaging the radiation image by irradiating a radiation to a subject and detecting an intensity of the transmitted radiation by a radiation detector has been known. Generally, in a hospital, a network has been constructed and various kinds of medical apparatuses are connected to the network and are interlocked with a hospital information system (HIS), a radiation information system (RIS), a medical image server, and the like.

In the imaging in the radiation imaging system, it is necessary to select an imaging condition prior to performing the imaging. Ordinarily, optimum image processing parameters differ in each combination every body part to be imaged and imaging position of a subject to be imaged and every type of radiation detector which is used for the imaging. The imaging condition is constructed by conditions having those information. For example, when the operator wants to perform the imaging under such conditions that a body part to be imaged is a chest region, an imaging position is a standing position, and a radiation detector A is used as a radiation detector, he selects the imaging condition having such information prior to imaging. The imaging condition is constructed by the following two kinds of information: that is, information of body part to be imaged (hereinafter, simply called body-part information); and combination information comprising imaging position information and type information of the radiation detector. In a setting display screen or the like, a setting of an association between the body-part information and each combination information can be performed. In an edition of the combination information, a change of the imaging position information and a setting of an association between the type information of the radiation detector and the inherent information of each radiation detector and the like can be also performed.

In the case of introducing a new radiation detector into the radiation imaging system, there is a case where associating work of the combination information and the body-part information (ordinarily, there are a number of body-part information) becomes a burden on the operator. On the other hand, Japanese Patent Application Laid-Open No. 2013-039198 discloses such an X-ray imaging control system that when combination information comprising imaging position information and type information of the radiation detector is newly formed, a burden on the operator is reduced by automatically performing the association between the combination information and each body-part information.

However, the technique disclosed in Japanese Patent Application Laid-Open No. 2013-039198 presumes a case where the combination information was newly formed. For example, in the case where a substitute apparatus is introduced when the radiation detector has broken down, in the case where another radiation detector is newly introduced, or the like, the operator needs to manually make the setting of association between the inherent information of the radiation detector and each combination information. Therefore, in the case of performing the association between the inherent information peculiar to the radiation detector and a plurality of combination information, since there are a plurality of combination information, there is a possibility that the associating work becomes a burden on the operator or it results in such a mistake that the operator forgets the association with specific combination information.

It is, therefore, an aspect of the invention to provide a technique which can reduce a working load and a mistake of the operator at the time of introducing a radiation detector.

SUMMARY OF THE INVENTION

According to an aspect of the invention, there is provided a control apparatus comprising: a processor coupled to a memory and programmed to function as: a display control unit configured to cause a display unit to display a selecting screen for presenting a list of registered radiation detectors and receiving a selection from the list; and an associating unit configured to associate in such a manner that when an unregistered radiation detector is registered, imaging information regarding a radiation imaging associated with the radiation detector selected through the selecting screen is associated with the unregistered radiation detector.

According to the invention, a technique which can reduce a working load and a mistake of the operator at the time of introducing a radiation detector can be provided.

Further features of the present invention will become apparent from the following description of exemplary embodiments with reference to the attached drawings.

BRIEF DESCRIPTION OF THE DRAWINGS

FIGS. 3A and 3B are diagrams (part 1) illustrating an example of a display screen of the radiation imaging system.

FIG. 6 is a diagram (part 2) illustrating an example of a display screen of the radiation imaging system.

FIG. 8 is a diagram (part 3) illustrating an example of a display screen of the radiation imaging system.

FIG. 10 is a diagram illustrating an example of substitute apparatus information in the embodiment 3.

FIGS. 12A and 12B are diagrams illustrating an example of log information and a log information display screen.

DESCRIPTION OF THE EMBODIMENTS

Preferred embodiments of the present invention will now be described in detail in accordance with the accompanying drawings.

Embodiment 1

1. Schematic Construction of Radiation Imaging System

Figure 1:
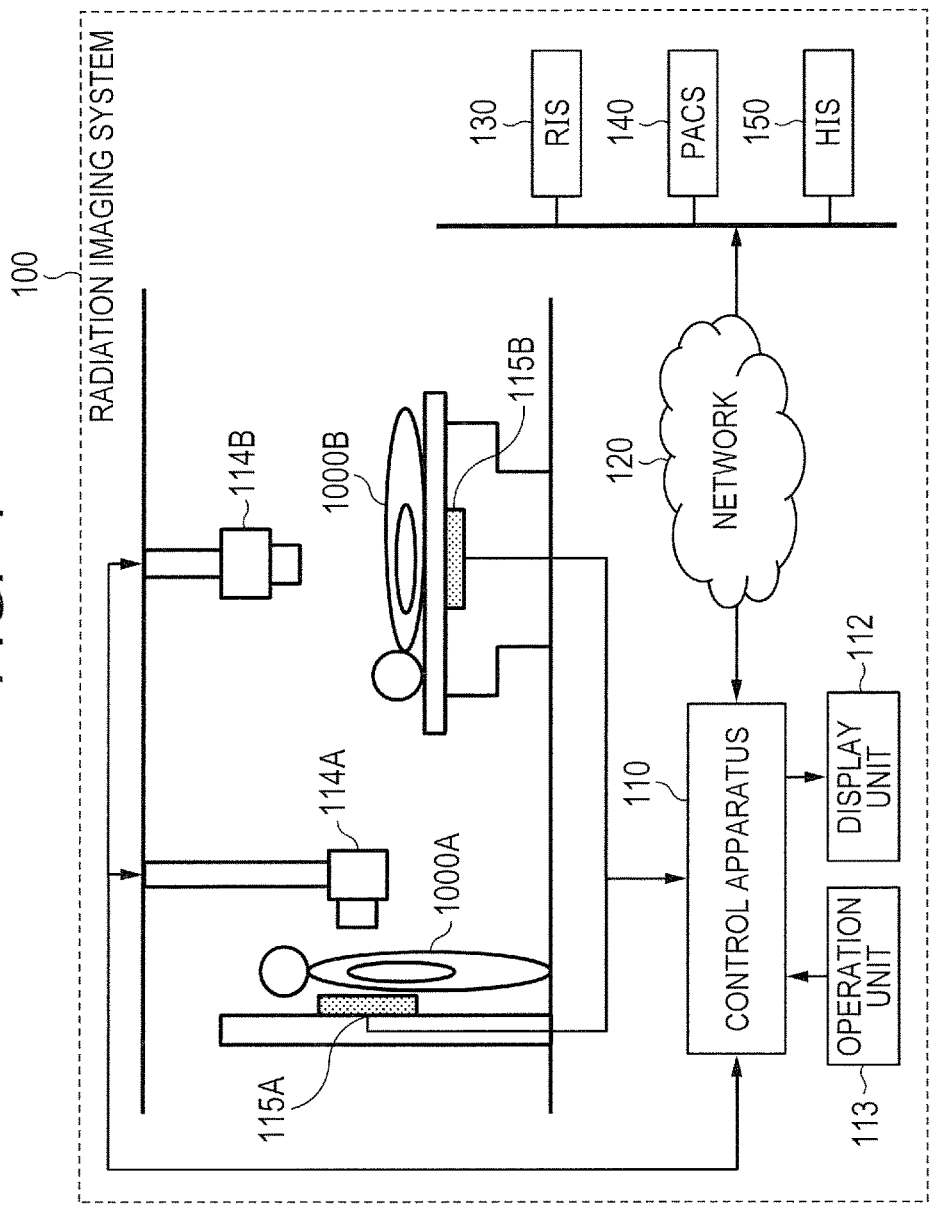
FIG. 1 is a diagram illustrating an example of a system construction of a radiation imaging system.

FIG. 1 is a diagram illustrating an example of a system construction of a radiation imaging system 100 in the embodiment. The radiation imaging system 100 has a control apparatus 110, radiation generating units 114A and 114B, radiation detectors 115A and 115B, a radiology information system (RIS) 130, an image server (PACS) 140, and a hospital information system (HIS) 150. In the following description, there is a case where the radiation generating units 114A and 114B are simply referred to as a radiation generating unit and the radiation detectors 115A and 115B are simply referred to as a radiation detector for simplicity of explanation.

The control apparatus 110 is connected to a display unit 112, an operation unit 113, the radiation generating units 114A and 114B, and the radiation detectors 115A and 115B by a wired or wireless manner and controls the operation of each unit. The control apparatus 110 is also connected to the radiology information system (RIS) 130, the image server (PACS) 140, and the hospital information system (HIS) 150 through a network 120 and can transmit and receive radiation images, patient information, and the like. The display unit 112 displays various kinds of information such as imaging inspection information, imaged radiation images, and the like. The operation unit 113 receives input information from the operator (user). In the embodiment, the display unit 112 is a monitor and the operation unit 113 is a keyboard, a mouse, or a touch panel.

The radiation generating units 114A and 114B have radiation tubes each for generating a radiation and irradiate the radiation to patients 1000A and 1000B as objects to be imaged. The patient 1000A is at a standing position and the patient 1000B is at a supine position. The radiation generating units 114A and 114B and the radiation detectors 115A and 115B are arranged at the positions suitable for imaging, respectively. The radiation detectors 115A and 115B detect the radiations irradiated from the radiation generating units 114A and 114B, respectively. The control apparatus 110 executes an image process to the radiation image data detected and obtained by the radiation detectors 115A and 115B and displays as radiation images to the display unit 112.

Although the radiation imaging system 100 in the embodiment will be described on the assumption that it includes the radiology information system (RIS) 130, the image server (PACS) 140, and the hospital information system (HIS) 150, such a construction that the system 100 does not include a part of them may be used. Although the case where the radiation generating units 114A and 114B and the radiation detectors 115A and 115B are used as a radiation generating unit and a radiation detector has been described in the example of FIG. 1, further another combination of the radiation generating units and the radiation detectors may be included in the radiation imaging system 100. Such a construction that the functions of the foregoing radiation imaging system 100 are realized by one apparatus may be used.

2. Construction of Control Apparatus

Figure 2A:
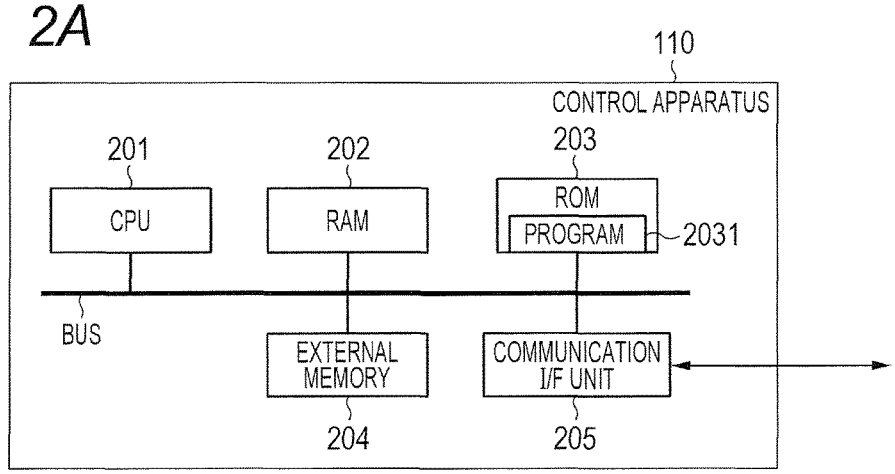
FIGS. 2A, 2B, and 2C are diagrams illustrating an example of a construction of a control apparatus and a radiation detector.

Subsequently, an example of the construction of the control apparatus 110 in the embodiment will now be described. FIG. 2A is a diagram illustrating an example of the hardware construction of the control apparatus 110. The control apparatus 110 has a CPU 201, a RAM 202, a ROM 203, an external memory (storage area) 204, and a communication I/F unit 205 and is mutually connected to them through a bus.

The CPU 201 unitedly controls the operation of the control apparatus 110 and controls each constructing unit (the RAM 202 to the communication I/F unit 205) illustrated in FIG. 2A through the bus. The RAM 202 functions as a main memory, a work area, and the like of the CPU 201. A program 2031 and the like which are necessary for the CPU 201 to execute the process has been stored in the ROM 203. The program 2031 may be stored in the external memory 204. The CPU 201 loads the necessary program 2031 from the ROM 203 or the like into the RAM 202 and executes it, thereby realizing a software construction of the control apparatus 110 and processes shown in flowcharts, which will be described hereinafter.

For example, various kinds of data, various kinds of information, and the like which are necessary when the CPU 201 executes processes using the program 2031 or the like have been stored in the external memory 204. For example, various kinds of data, various kinds of information, and the like which are obtained after the CPU 201 executed the processes using the program 2031 or the like are stored in the external memory 204. The communication I/F unit 205 communicates with an outside. The bus connects the CPU 201 to the RAM 202, ROM 203, external memory 204, and communication I/F unit 205 so that it can communicate with each other.

Figure 2B:
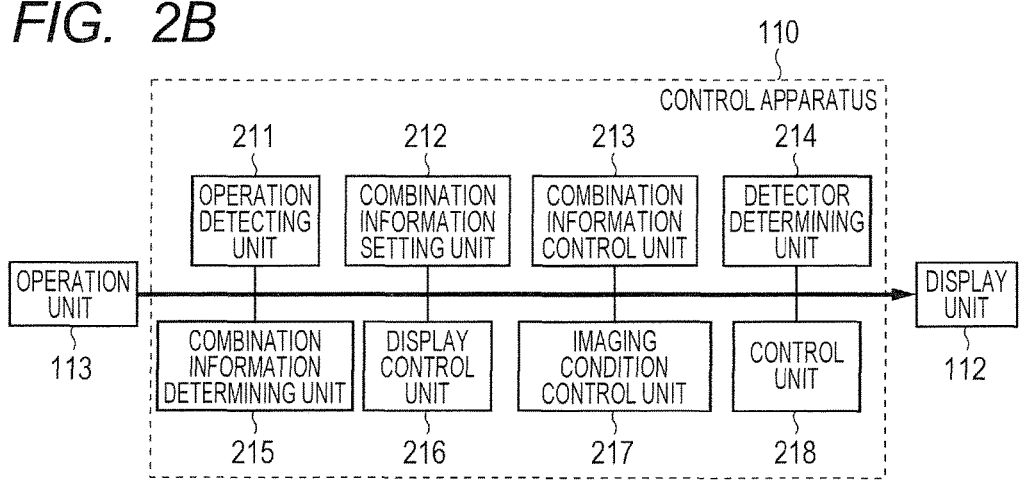

FIG. 2B is a diagram illustrating an example of a software construction of the control apparatus 110 in the embodiment. The control apparatus 110 has an operation detecting unit 211, a combination information setting unit 212, a combination information control unit 213, a detector determining unit 214, a combination information determining unit 215, a display control unit 216, an imaging condition control unit 217, and a control unit 218. As mentioned above, each function of those units is realized when the CPU 201 develops the program stored in the ROM 203 into the RAM 202 and executes it.

The operation detecting unit 211 detects the user operation executed through the operation unit 113. The combination information setting unit 212 forms and edits combination information comprising type information of a radiation detector which is used in the radiation imaging system 100 and imaging position information of a patient. In the present embodiment and subsequent embodiments, a description will be made on the assumption that the combination information comprises the type information of the radiation detector and the imaging position information. However, information included in the combination information is not limited to such information. For example, the combination information may be such information (imaging information) that information regarding imaging conditions such as body part to be image and imaging position of the patient, information regarding image processing conditions, and the like are associated with the type information of the radiation detector.

The combination information control unit 213 associates the combination information set by the combination information setting unit 212 with inherent information peculiar to each radiation detector. "Inherent information" mentioned here denotes, for example, a serial number or the like of each radiation detector and is information which can unconditionally identify the radiation detector. The detector determining unit 214 specifies the radiation detector and the type information of the radiation detector. The combination information determining unit 215 discriminates the presence or absence of the combination information set in the radiation imaging system 100. The display control unit 216 displays a screen regarding the setting in the combination information setting unit 212 to the display unit 112, displays an imaged radiation image to the display unit 112, or displays an image corresponding to the operation executed through the operation unit 113 and detected by the operation detecting unit 211 to the display unit 112.

The imaging condition control unit 217 associates the body-part information with the combination information set by the combination information setting unit 212. The control unit 218 discriminates the presence or absence of various kinds of setting information set in the radiation imaging system 100, and forms and edits them. Each of the foregoing software constructions is merely shown as an example. The control apparatus 110 may have such a construction that it does not include a part of the functions in each of the foregoing software constructions or may have a software construction including further other functions.

3. Construction of Radiation Detector

Figure 2C:
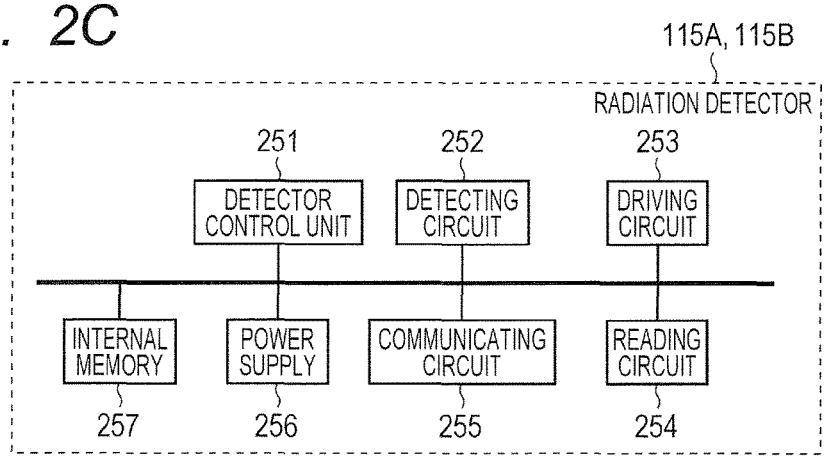

Subsequently, an example of a construction of each of the radiation detectors 115A and 115B in the embodiment will be described. FIG. 2C is a diagram illustrating an example of a hardware construction of each of the radiation detectors 115A and 115B. Each of the radiation detectors 115A and 115B has a detector control unit 251, a detecting circuit 252, a driving circuit 253, a reading circuit 254, a communicating circuit 255, a power supply 256, and an internal memory (storage area) 257.

The detector control unit 251 unitedly controls each unit. The detecting circuit 252 monitors an output of a radiation sensor and detects an irradiation of the radiation. The driving circuit 253 drives the radiation sensor in an accumulating state or a read-out state. For example, the detector control unit 251 instructs the driving circuit 253 to start the accumulating state on the basis of the detection of the radiation irradiation in the detecting circuit 252, and the driving circuit 253 drives the radiation sensor in the read-out state in response to such an instruction.

The reading circuit 254 amplifies the signal read out by the driving circuit 253, A/D converts, and outputs radiation image data. The communicating circuit 255 transmits the radiation image data output from the reading circuit 254 and receives a control signal from the control apparatus 110. The power supply 256 supplies an electric power to each component element. The radiation detectors 115A and 115B control the operation in response to the control signal received from the control apparatus 110. For example, such information that it will be understood that the detector is a substitute apparatus of the radiation detector 115A or the like has been stored in the internal memory 257.

4. Example of Combination Information Setting Screen

FIG. 3A is a diagram illustrating an example of a combination information setting screen 301 which is displayed to the display unit 112 in the embodiment. The combination information setting screen 301 has a combination information display area 302, an addition instructing area 303, a deletion instructing area 304, a combination information details display area 305, a combination name setting area 306, an imaging position selecting area 307, a detector type selecting area 308, and a color information selecting area 309. Further, the combination information setting screen 301 has a registered detector display area 310, a setting completion instructing area 311, and a setting cancellation instructing area 312.

The combination information display area 302 displays a list of the combination information set in the radiation imaging system 100. A name of the combination information and type information and imaging position information of the radiation detector are displayed on the list of the combination information. The addition instructing area 303 is a button to newly form combination information. The deletion instructing area 304 is a button to delete the combination information selected by the combination information display area 302. If nothing is selected in the combination information display area 302, the button is invalid.

Details of the combination information selected by the combination information display area 302 are displayed in the combination information details display area 305. The combination name setting area 306 is an area in which the name of the combination information has been displayed. The combination name setting area 306 is constructed by a text box and the like and the name of the combination information can be changed through the operation unit 113 such as a keyboard or the like. The imaging position selecting area 307 is an area in which the imaging position information of the combination information can be displayed and changed and it can be selected from the list of the imaging position information such as combo boxes or the like. The detector type selecting area 308 is an area in which the type of radiation detector in the combination information can be displayed and changed and it can be selected from the list of the type information such as combo boxes or the like. The color information selecting area 309 is an area in which, when imaging conditions are displayed on the imaging screen, a color is set every combination information in such a manner that the operator can easily discriminate the imaging conditions, and it can be selected from the list of the color information such as combo boxes or the like.

The registered detector display area 310 is an area in which a list of the radiation detectors registered in the radiation imaging system 100 is displayed. A check box to discriminate whether or not the radiation detector has been associated with the combination information and the name, serial number, and type information of each radiation detector are displayed on the list of the radiation detectors. By checking the check box, the radiation detector can be associated with the combination information displayed in the combination information details display area 305. At this time, if the type information of the radiation detector to be associated and the type information displayed in the detector type selecting area 308 differ, the check box cannot be checked. The setting completion instructing area 311 is a button to instruct a decision of the setting contents of the combination information. The setting cancellation instructing area 312 is a button to instruct a cancellation of the change contents of the setting of the combination information.

5. Example of Combination Information Newly-Forming Screen

FIG. 3B is a diagram illustrating an example of a combination information newly-forming screen 313 which is displayed in the display unit 112 when the button of the addition instructing area 303 displayed in the combination information setting screen 301 has been depressed. The combination information newly-forming screen 313 has a combination name setting area 314, an imaging position selecting area 315, a detector type selecting area 316, a color information selecting area 317, a registered detector display area 318, a setting completion instructing area 319, and a setting cancellation instructing area 320.

The combination name setting area 314 is an area to set the name of the combination information and is constructed by a text box and the like, and the name of the combination information can be set through the operation unit 113 such as a keyboard or the like. The imaging position selecting area 315 is an area in which the imaging position information of the combination information can be set, and it can be selected from the list of the imaging position information such as combo boxes or the like. The detector type selecting area 316 is an area in which the type information of the radiation detector in the combination information can be set, and it can be selected from the list of the type information such as combo boxes or the like. The color information selecting area 317 is an area in which when imaging conditions are displayed on the imaging screen, a color is set every combination information in such a manner that the operator can easily discriminate the imaging conditions, and it can be selected from the list of the color information such as combo boxes or the like.

The registered detector display area 318 is an area in which a list of the radiation detectors registered in the radiation imaging system 100 is displayed. A check box to associate the radiation detector with the combination information and the name, serial number, and type information of each radiation detector are displayed on the list of the radiation detectors. By checking the check box, the radiation detector can be associated with the combination information which is being formed. At this time, if the type information of the radiation detector to be associated and the type information displayed in the detector type selecting area 316 differ, the check box cannot be checked. The setting completion instructing area 319 is a button to instruct a determination of the forming contents of the combination information. If at least one or more of the check boxes in the registered detector display area 318 are not checked, the button is invalid. The setting cancellation instructing area 320 is a button to instruct a cancellation of the forming of the combination information.

The operator can select and instruct each button or the like through the operation unit 113. Or, if the display unit 112 is a touch panel, each button or the like may be selected and instructed by directly touching the combination information setting screen 301 or the combination information newly-forming screen 313.

6. Example of Automatic Associating Process

Figure 4:
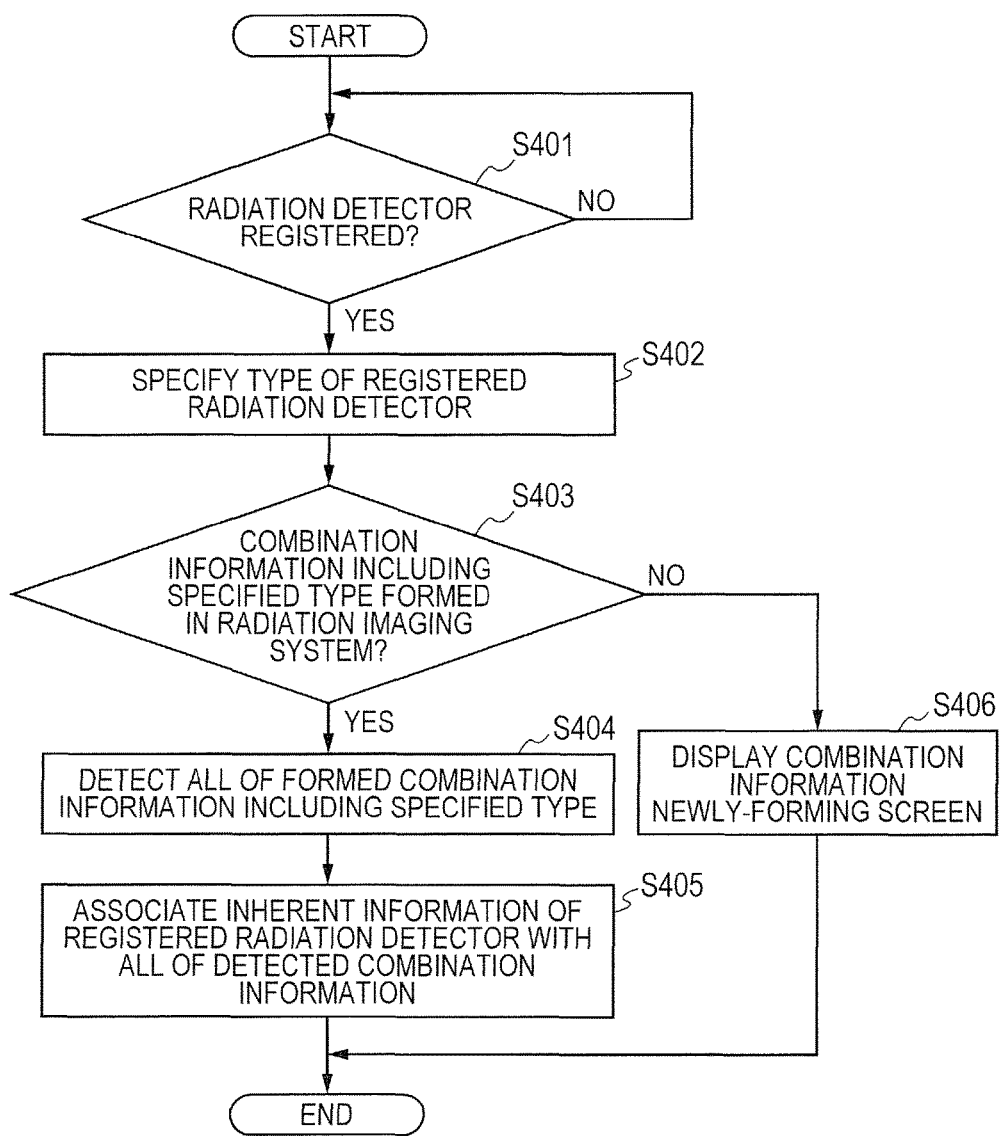
FIG. 4 is a flowchart (part 1) illustrating an example of a process of the embodiment 1.

FIG. 4 is a flowchart illustrating an example of such a process that, when the radiation detector is registered into the radiation imaging system 100 in the embodiment, the control apparatus 110 associates the registered radiation detectors with the combination information.

In S401, the control unit 218 discriminates whether or not an unregistered radiation detector has been registered into the radiation imaging system 100. If the control unit 218 determines that the unregistered radiation detector has been registered, the processing routine advances to S402. If the control unit 218 determines that the unregistered radiation detector is not registered, the apparatus waits until it is registered. In S402, the detector determining unit 214 specifies the type information of the registered radiation detector.

In S403, the combination information determining unit 215 discriminates whether or not the combination information including the type information of the radiation detector specified in S402 has already been formed in the radiation imaging system 100. If the combination information determining unit 215 determines that such combination information has been formed, S404 follows. If the combination information determining unit 215 determines that such combination information is not formed, S406 follows.

In S404, the combination information control unit 213 detects all of the combination information including the type information of the radiation detector specified in S402. In S405, the combination information control unit 213 associates the inherent information such as a serial number and the like of the registered radiation detector with all of the combination information detected in S404. In S406, the display control unit 216 displays the combination information newly-forming screen 313 onto the display unit 112. The process in S406 is an example of a formed screen displaying process for displaying the combination information newly-forming screen 313. In this manner, each process in the flowchart of FIG. 4 is finished.

As described above, in the embodiment, when the radiation detector is introduced, the control apparatus 110 automatically associates the inherent information of the radiation detector with the combination information including the type information of the radiation detector. At this time, if there is no combination information including the type information, the control apparatus 110 displays the combination information newly-forming screen 313. Thus, omission of the association due to a working load and a mistake of the association between the inherent information of the radiation detector and the combination information by the operator at the time of introducing the radiation detector can be reduced.

[Modification 1]

In the modification 1, a rule for associating the inherent information of the radiation detector and the combination information (associating rule) and a forming rule at the time of automatically forming combination information (combination information automatic forming rule) are preliminarily set. An example in which an association between the inherent information of the radiation detector and the combination information according to an intention of the operator is performed on the basis of those rule settings will be described. A construction of the radiation imaging system 100, control apparatus 110, and the like is similar to that described in the embodiment 1.

Figure 5:
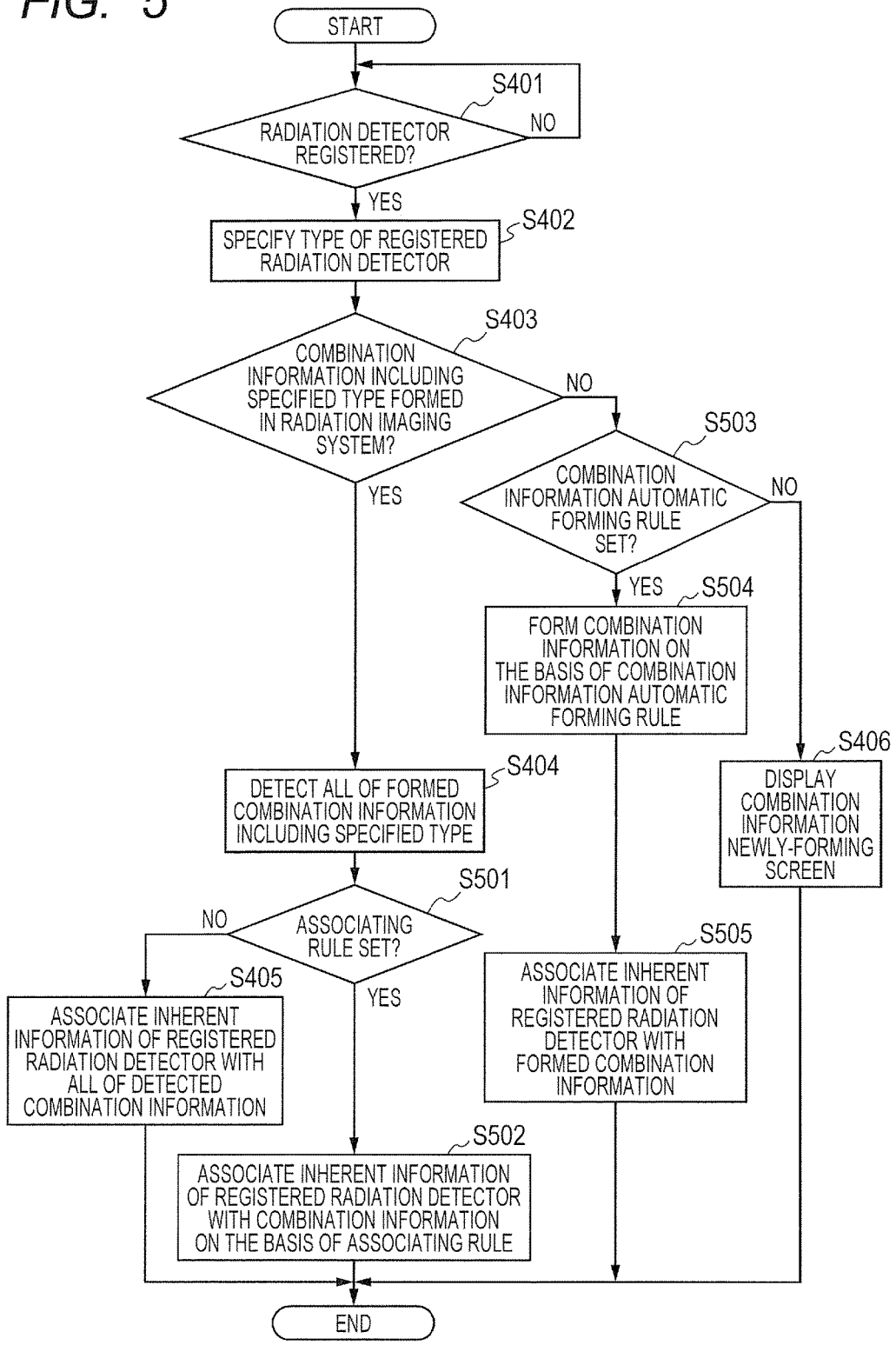
FIG. 5 is a flowchart (part 2) illustrating an example of the process of the embodiment 1.

FIG. 5 is a flowchart illustrating an example of such a process that the control apparatus 110 performs an association between the inherent information of the radiation detector and the combination information on the basis of the associating rule and the combination information automatic forming rule. Processes similar to those in FIG. 4 are designated by the same processing steps and their description is omitted here.

In S501, the control unit 218 discriminates whether or not the associating rule has already been set in the radiation imaging system 100. "Associating rule" mentioned here is such a rule that, for example, the radiation detector using radio communication is not associated with the combination information including the imaging position information in which the imaging position is a supine position, or the like. If the control unit 218 determines that the associating rule has already been set in the radiation imaging system 100, S502 follows. If it is determined that the associating rule is not set yet, S405 follows. In S502, the combination information control unit 213 associates the inherent information of the registered radiation detector with the combination information detected in S404 on the basis of the associating rule.

In S503, the control unit 218 discriminates whether or not the combination information automatic forming rule has already been set in the radiation imaging system 100. For example, the combination information automatic forming rule is such a rule that a default name is assumed to be "Workspace" and a forming method of the combination information whereby a character train of the type and imaging position of the radiation detector is added to the end or the like has been predetermined. The combination information automatic forming rule may be such a rule that a plurality of combination information of different conditions are formed. If the control unit 218 determines that the combination information automatic forming rule has already been set, S504 follows. If it is determined that the combination information automatic forming rule is not set, S406 follows.

In S504, the combination information setting unit 212 forms combination information on the basis of the combination information automatic forming rule. In S505, the combination information control unit 213 associates the inherent information of the registered radiation detector with the combination information formed in S504.

As described above, in the modification 1, the associating rule and the combination information automatic forming rule are used. Thus, in the automatic associating process, there is such an effect that the association between the inherent information of the radiation detector and the combination information according to the intention of the operator can be realized.

Embodiment 2

In the embodiment 1, the example in which when the radiation detector is registered, the association between the combination information and the inherent information of the radiation detector is automatically performed has been described. On the other hand, in the embodiment 2, before the radiation detector is registered, the operator previously selects the radiation detector which has already been registered in the radiation imaging system 100. An example in which an association between the combination information associated with the selected radiation detector and the inherent information of the radiation detector to be registered is performed will now be described.

Generally, when the radiation detector which has been used so far cannot be used due to a breakdown or the like and it is necessary to use a substitute apparatus, it is desirable that the combination information which is associated with the substitute apparatus is equal to that of the radiation detector which has been used so far. In the embodiment 2, an example in which when the substitute apparatus is used due to a breakdown or the like of the radiation detector which has been used so far, combination information which is almost equivalent to the combination information associated with the radiation detector which has been used so far can be easily associated will be described. Since a construction of the radiation imaging system 100, control apparatus 110, and the like in the embodiment is similar to that in the embodiment 1, its description is omitted here.

FIG. 6 is a diagram illustrating an example of a radiation detector selecting screen 601 which is displayed in the display unit 112 in the embodiment 2. The radiation detector selecting screen 601 has a radiation detector list display area 602, a selection completion instructing area 603, and a selection cancellation instructing area 604.

The radiation detector list display area 602 displays a list of the radiation detectors registered in the radiation imaging system 100. Check boxes each for selecting the radiation detector, a name of each radiation detector, associated combination information, type information of the radiation detector, and a serial number are displayed on the list of the radiation detectors. To select the radiation detector, an arbitrary one of the check boxes is checked.

The selection completion instructing area 603 is a button to instruct a determination of the selection contents of the radiation detector. When the button of the area 603 is depressed, the control apparatus 110 associates the combination information associated with the selected radiation detector with the radiation detector which is registered. If any one of the check boxes in the radiation detector list display area 602 is not checked, the button is invalid. The selection cancellation instructing area 604 is a button to instruct a cancellation of the selection of the radiation detector.

Figure 7:
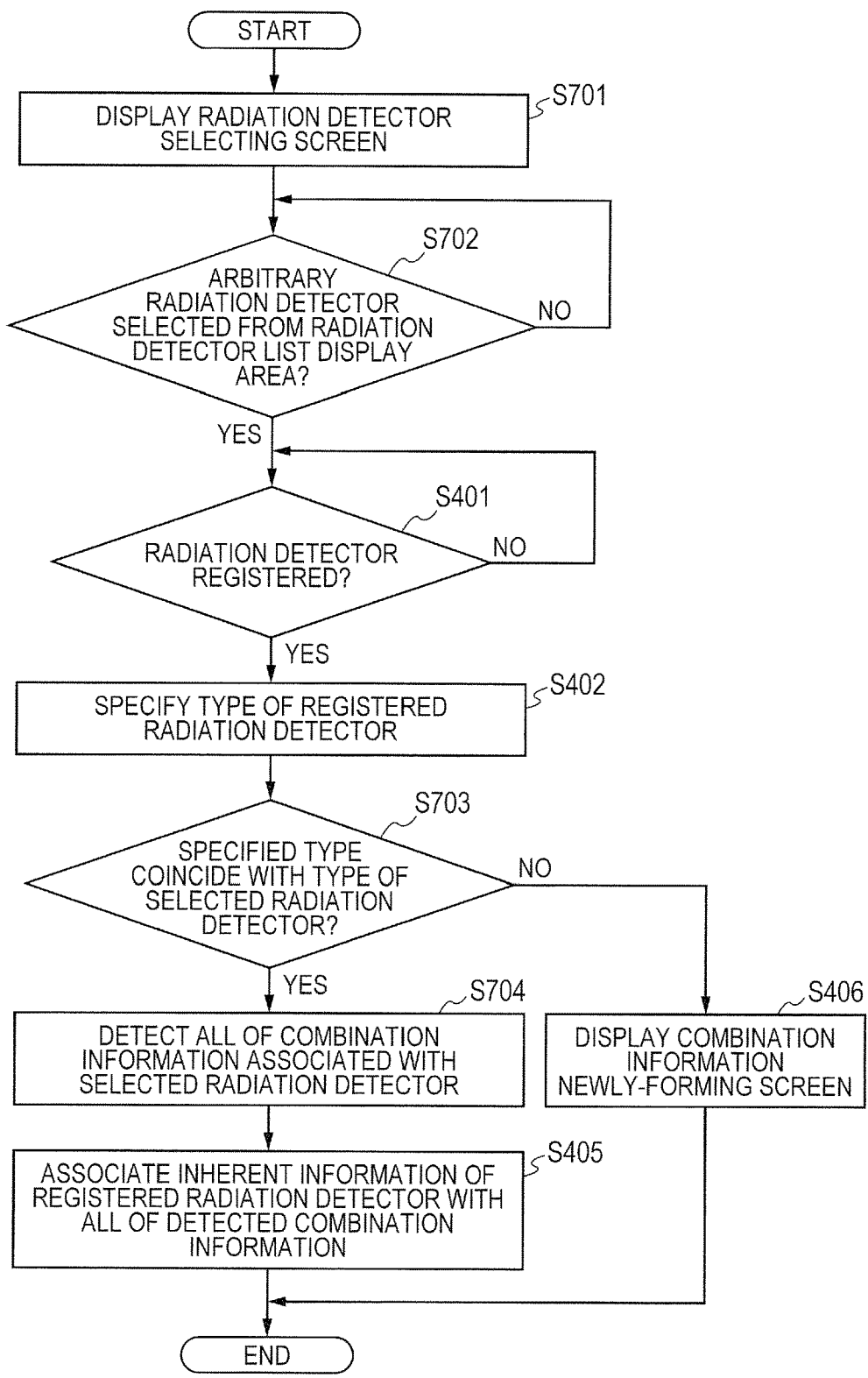
FIG. 7 is a flowchart (part 1) illustrating an example of a process of the embodiment 2.

FIG. 7 is a flowchart illustrating an example of a process by the control apparatus 110 for associating the inherent information of the radiation detector with the combination information on the basis of a result of the selection of the radiation detector selecting screen 601 which was performed by the operator. Processes similar to those in FIG. 4 are designated by the same processing steps and their description is omitted here.

In S701, the display control unit 216 displays the radiation detector selecting screen 601 to the display unit 112. The process in S701 is an example of a displaying process for displaying the radiation detector selecting screen 601 on which the list of the registered radiation detectors is displayed. In S702, the operation detecting unit 211 discriminates whether or not a depression of the button of the selection completion instructing area 603 has been detected. If the operation detecting unit 211 determines that the button of the selection completion instructing area 603 has been depressed, S401 follows. If it is determined that the button is not depressed, the apparatus waits until the button of the selection completion instructing area 603 is depressed.

In S703, the detector determining unit 214 discriminates whether or not the type information of the radiation detector specified in S402 and the type information of the radiation detector selected in S702 are equal. If the detector determining unit 214 determines that they are equal, S704 follows. If it is determined that they differ, S406 follows. In S704, the combination information determining unit 215 detects all of the combination information associated with the radiation detector selected in S702. In this manner, each process of the flowchart of FIG. 7 is finished.

As described above, in the embodiment 2, before the radiation detector is registered, the operator preliminarily selects the radiation detector which has already been registered in the radiation imaging system 100. The control apparatus 110 associates the combination information associated with the selected radiation detector with the inherent information of the radiation detector which is registered. Thus, when it is necessary to use the substitute apparatus in place of the radiation detector which has been used so far due to a breakdown or the like, the same combination information as that of the radiation detector which has been used so far can be easily associated with the substitute apparatus, and there is such an effect that a time which is required until the substitute apparatus can be used is shortened.

[Modification 2]

In the example of the embodiment 2, in the case of using the substitute apparatus of the radiation detector due to a breakdown or the like, the type of the radiation detector as a substitute apparatus is the same as that of the radiation detector before it is substituted. However, there is a case where the substitute apparatus of the same type does not exist and a radiation detector of a new type is used as a substitute apparatus in dependence on a situation. Even in such a case, it is desirable that the combination information which is associated with the radiation detector of the new type is the combination information of the same type as that of the radiation detector which has been used so far.

Therefore, in the modification 2, an example in which in the case where the radiation detector of every new type different from the types of the registered radiation detectors is registered in the radiation imaging system 100, an association between the inherent information of the radiation detector of every new type and the combination information is performed will be described. A construction of the radiation imaging system 100, control apparatus 110, and the like is similar to that described in the embodiment 1.

FIG. 8 is a diagram illustrating an example of a combination information selecting screen 801 which is displayed in the display unit 112 in the modification 2. The combination information selecting screen 801 has a combination information list display area 802, a combination information selection completion display area 803, and a combination information selection cancellation display area 804. The combination information list display area 802 displays a list of the combination information set in the radiation imaging system 100. Check boxes each for selecting the combination information, a name of each combination information, an imaging position, a type of radiation detector, and color information are displayed on the list of the combination information. To select the combination information, at least one or more of the check boxes are checked.

The combination information selection completion display area 803 is a button to instruct a determination of the selection contents of the combination information. When the button of the area 803 is depressed, the control apparatus 110 newly forms combination information on the basis of the settings of the selected combination information and associates with the radiation detector which is registered. If any one of the check boxes of the combination information list display area 802 is not checked, the button is invalid. The combination information selection cancellation display area 804 is a button to instruct a cancellation of the selection of the radiation detector.

Figure 9:
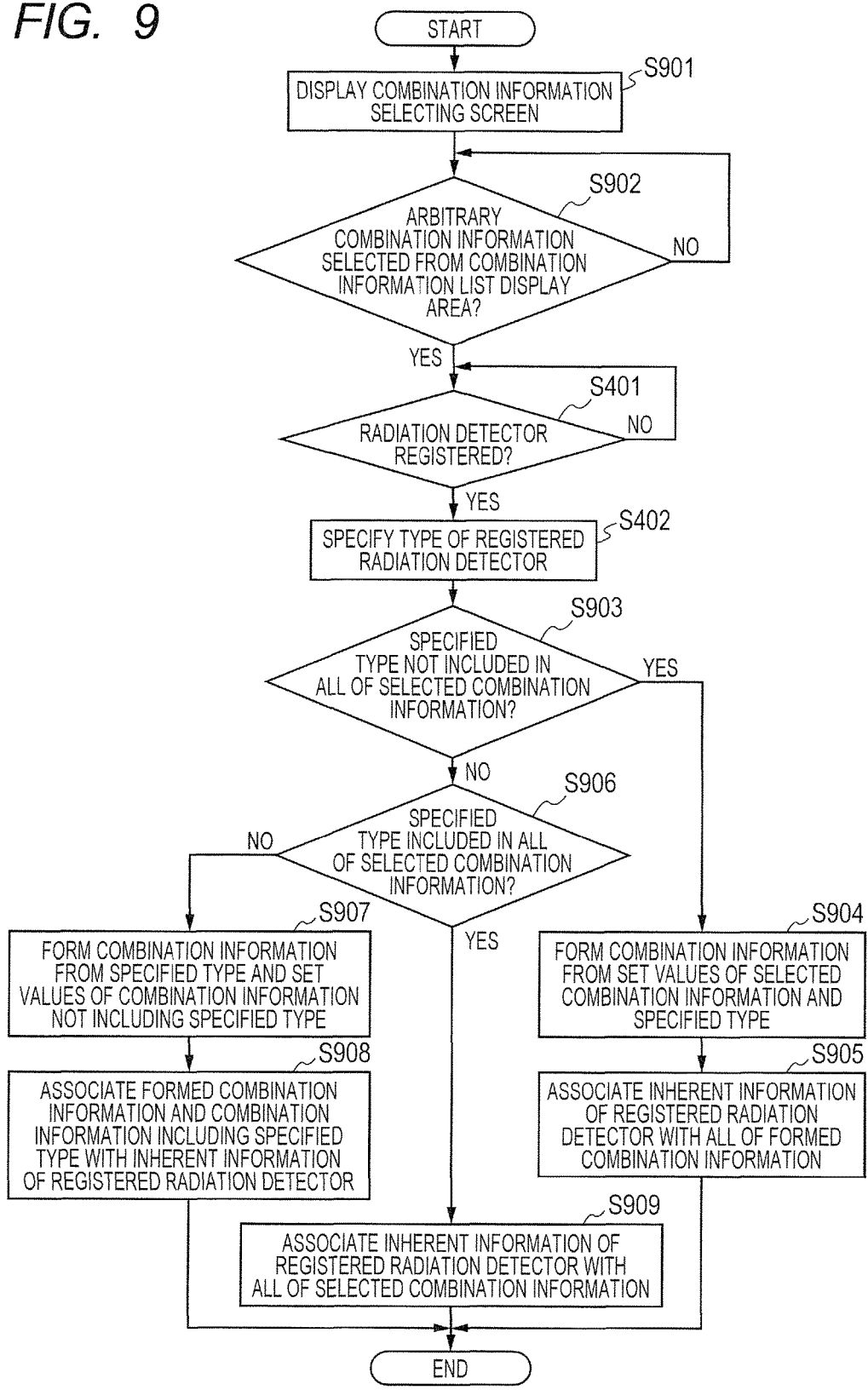
FIG. 9 is a flowchart (part 2) illustrating an example of the process of the embodiment 2.

FIG. 9 is a flowchart illustrating an example of the process by the control apparatus 110 for performing an association between the inherent information of the radiation detector and the combination information on the basis of a result of the selection of the combination information selecting screen 801 which was performed by the operator. Processes similar to those in FIG. 4 are designated by the same processing steps and their description is omitted here.

In S901, the display control unit 216 displays the combination information selecting screen 801 to the display unit 112. The process in S901 is an example of a selecting screen displaying process for displaying the combination information selecting screen 801 on which the list of the combination information is displayed. In S902, the operation detecting unit 211 discriminates whether or not a depression of the button of the combination information selection completion display area 803 has been detected. If the operation detecting unit 211 determines that the button of the combination information selection completion display area 803 has been depressed, S401 follows. If it is determined that the button is not depressed, the apparatus waits until the button of the combination information selection completion display area 803 is depressed.

In S903, the combination information determining unit 215 discriminates whether or not the type information of the radiation detector specified in S402 is not included in the combination information selected in the combination information list display area 802. If the combination information determining unit 215 determines that the type information is not included, S904 follows. If it is determined that the type information is included, S906 follows. In S904, the combination information setting unit 212 forms combination information comprising setting values (for example, the imaging position is a standing position and the color information is orange) of the selected combination information and the type information specified in S402. In S905, the combination information control unit 213 associates the inherent information of the registered radiation detector with the combination information formed in S904.

In S906, the combination information determining unit 215 discriminates whether or not the type information of the radiation detector specified in S402 is included in all of the combination information selected in the combination information list display area 802. If the combination information determining unit 215 determines that the type information is not included in all of the combination information, S907 follows. If it is determined that the type information is included in all of the combination information, S909 follows.

In S907, the combination information setting unit 212 forms combination information comprising setting values of the combination information not including the type information of the radiation detector specified in S402 in the selected combination information and the specified type information. In S908, the combination information control unit 213 associates the combination information including the formed combination information and the type information of the specified radiation detector with the inherent information of the registered radiation detector. On the other hand, in S909, the combination information control unit 213 associates the inherent information of the registered radiation detector with all of the selected combination information. In this manner, each process of the flowchart in FIG. 9 is finished.

As described above, in the modification 2, the control apparatus 110 forms and associates combination information on the basis of the settings of the existing combination information. Thus, in the automatic associating process, there is such an effect that when the radiation detector of every new type is added as a substitute apparatus to the radiation imaging system 100 due to a breakdown or the like, the combination information which is almost equivalent to the combination information associated with the radiation detector which has been used so far can be associated.

Embodiment 3

In the embodiment 3, information showing that the radiation detector is the substitute apparatus is stored in the internal memory 257 of the radiation detector. An example in which when the radiation detector is registered into the radiation imaging system 100, the control apparatus 110 automatically associates the inherent information of the radiation detector with the combination information with reference to such information will be described.

In the embodiment 2, when the substitute apparatus of the radiation detector is used due to a breakdown or the like, it is necessary that the combination information which is associated with the substitute apparatus is set to the combination information which is almost equivalent to that of the radiation detector which has been used so far. Therefore, the operator can associate with the equivalent combination information by selecting a substitution-target radiation detector or preliminarily selecting the combination information. However, when a plurality of radiation detectors have been registered in the radiation imaging system 100, it is necessary to search for the desired radiation detector from them. There is also a case where it takes a time for the manual selecting operation by the operator.

In the embodiment 3, an example in which those manual operations by the operator are reduced and the inherent information of the radiation detector and the combination information are more easily associated will now be described. Since a construction of the radiation imaging system 100, control apparatus 110, and the like in the embodiment is similar to that in the embodiment 1, its description is omitted here.

FIG. 10 is a diagram illustrating an example of substitute apparatus information 1001 stored in the internal memory 257. The substitute apparatus information 1001 comprises: information showing whether or not a substitution can be performed; and information such as name, serial number, and the like of the substitution-target radiation detector. Those information may be set at the time of factory shipping or may be set through the operation unit 113 or network 120.

Figure 11:
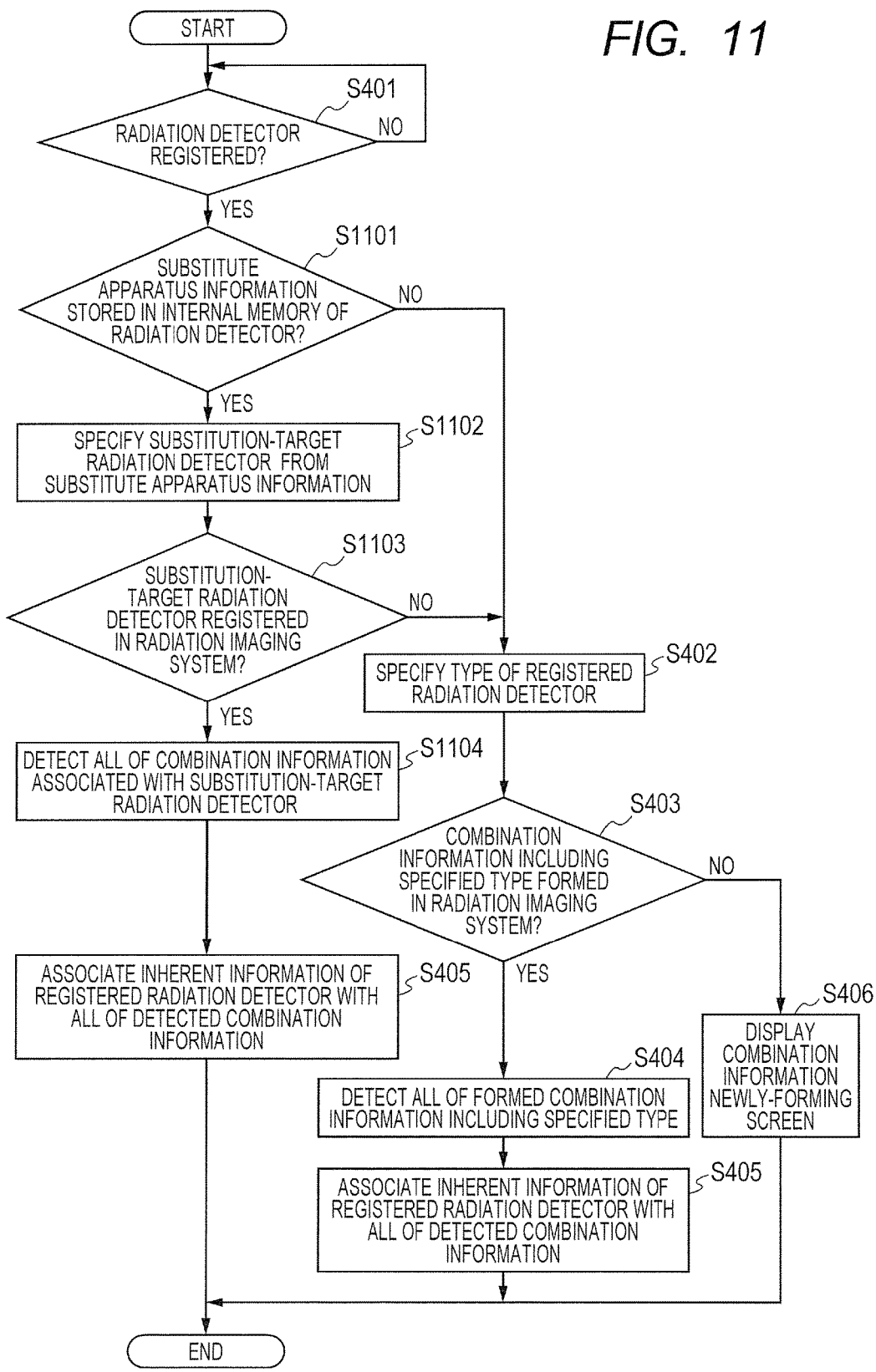
FIG. 11 is a flowchart illustrating an example of a process of the embodiment 3.

FIG. 11 is a flowchart illustrating an example of such a process that the control apparatus 110 automatically associates the inherent information of the radiation detector with the combination information on the basis of the substitute apparatus information 1001 stored in the internal memory 257 of the radiation detector. Processes similar to those in FIG. 4 are designated by the same processing steps and their description is omitted here.

In S1101, the control unit 218 discriminates whether or not the substitute apparatus information 1001 has been stored in the internal memory 257 of the registered radiation detector. If the control unit 218 determines that the substitute apparatus information 1001 has been stored, S1102 follows. If it is determined that the substitute apparatus information 1001 is not stored, S402 follows. In S1102, the control unit 218 specifies the substitution-target radiation detector from the substitute apparatus information 1001. In S1103, the detector determining unit 214 discriminates whether or not the radiation detector specified in S1102 has been registered in the radiation imaging system 100. If the detector determining unit 214 determines that the radiation detector has been registered, S1104 follows. If it is determined that the radiation detector is not registered, S402 follows. In S1104, the combination information determining unit 215 detects all of the combination information associated with the substitution-target radiation detector. In this manner, each process of the flowchart of FIG. 11 is finished.

As described above, in the embodiment 3, the control apparatus 110 associates the inherent information of the radiation detector with the combination information on the basis of the substitute apparatus information stored in the internal memory 257. Thus, the combination information can be easily associated with the substitute apparatus and there is such an effect that a working load accompanied with the selecting work or the like of the substitution-target radiation detector which is performed by the operator is reduced.

Embodiment 4

In the embodiment 4, the substitution-target radiation detector stores information of the substitution-target radiation detector into the external memory 204. An example in which when the substitute apparatus is registered into the radiation imaging system 100, the control apparatus 110 automatically associates the inherent information of the radiation detector with the combination information with reference to such information will be described. Since a construction of the radiation imaging system 100, control apparatus 110, and the like in the embodiment is similar to that in the embodiment 1, its description is omitted here.

FIG. 12A is a diagram illustrating an example of log information (recording information) 1201 stored in the external memory 204 in the embodiment 4. The log information 1201 comprises: a list of the combination information associated with the substitution-target radiation detector; and information such as name, type information, and the like of the radiation detector.

FIG. 12B is a diagram illustrating an example of a log information screen 1221 which is displayed to the display unit 112 in the embodiment 4. The log information screen 1221 has a log information list display area 1222, a completion instructing area 1223, and a cancellation instructing area 1224. A list of the log information 1201 stored in the external memory 204 is displayed in the log information list display area 1222. The completion instructing area 1223 is a button to instruct an association between the combination information displayed in the log information list display area 1222 and the inherent information of the registered radiation detector. The cancellation instructing area 1224 is a button to instruct that the association with the combination information displayed in the log information list display area 1222 is not performed.

Figure 13:
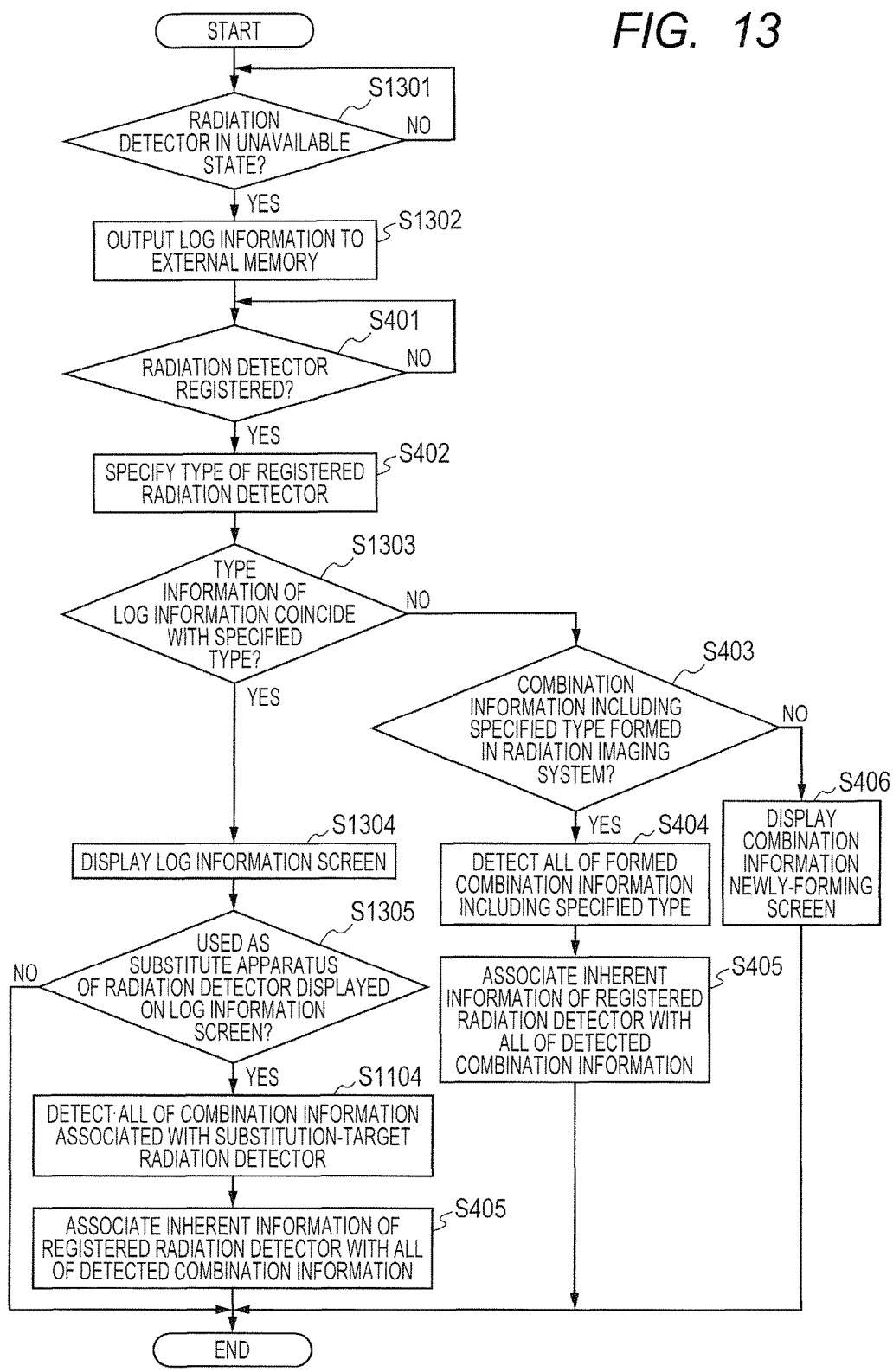
FIG. 13 is a flowchart illustrating an example of a process of the embodiment 4.

FIG. 13 is a flowchart illustrating an example of such a process that the control apparatus 110 automatically associates the inherent information of the radiation detector with the combination information on the basis of the log information 1201 stored in the external memory 204. Processes similar to those in FIGS. 4 and 11 are designated by the same processing steps and their description is omitted here.

In S1301, the detector control unit 251 monitors a state of the radiation detector during use of the radiation detector and discriminates whether or not the radiation detector is in an unavailable state. If the detector control unit 251 determines that the radiation detector is in the unavailable state, S1302 follows. If it is determined that the radiation detector is in an available state, the detector control unit 251 continues the monitoring of the state of the radiation detector. In S1302, the detector control unit 251 stores the log information 1201 into the external memory 204. In S1303, the control unit 218 discriminates whether or not the type information of the radiation detector included in the log information 1201 and the type information specified in S402 are equal. If the control unit 218 determines that they are equal, S1304 follows. If it is determined that they differ, S403 follows.

In S1304, the display control unit 216 displays the log information screen 1221 to the display unit 112. The process in S1304 is an example of a recording information screen displaying process for displaying the log information screen (recording information screen) 1221 on which the log information (recording information) 1201 is presented. In S1305, the operation detecting unit 211 detects the operation of the operator through the log information screen 1221 and discriminates whether or not any instruction which shows whether or not the radiation detector is used as a substitute apparatus of the radiation detector and was displayed on the log information screen 1221 has been received. If the operation detecting unit 211 determines that the instruction for allowing the operator to use the radiation detector as a substitute apparatus has been received, S1104 follows. If it is determined that such an instruction that the operator does not use the radiation detector as a substitute apparatus has been received, the processing routine is finished. In this manner, each process of the flowchart of FIG. 13 is finished.

As described above, in the embodiment 4, the control apparatus 110 associates the inherent information of the radiation detectors with the combination information on the basis of the log information stored in the external memory 204. Thus, the combination information can be easily associated with the substitute apparatus and there is such an effect that a working load accompanied with the selecting work or the like of the substitution-target radiation detector which is performed by the operator is reduced.

Other Embodiments

According to the embodiments mentioned above, the technique which can reduce the working load and mistake of the operator at the time of introducing the radiation detector can be provided.

Embodiment(s) of the present invention can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-037334, filed Feb. 26, 2015, which is hereby incorporated by reference herein in its entirety.

What is claimed is:

1. A control apparatus comprising:
   a processor coupled to a memory and programmed to function as:
   a display control unit configured to cause a display unit to display a selecting screen for presenting a list of imaging information of registered radiation detectors and receiving a selection from the list, the imaging information being information in which information regarding a radiation imaging is associated with type information of each radiation detector; and
   an associating unit configured to associate in such a manner that when a certain radiation detector is registered, the imaging information selected through the selecting screen is associated with inherent information of the certain radiation detector, the inherent information being information capable of identifying the certain radiation detector.

2. The control apparatus according to claim 1, further comprising a determining unit configured to determine whether or not the type information of the certain radiation detector and the type information of the radiation detector associated with the selected imaging information are equal,
   wherein if it is determined by the determining unit that they are equal, the associating unit is configured to associate the selected imaging information with the inherent information of the certain radiation detector.

3. The control apparatus according to claim 2, wherein the display control unit is configured to cause the display unit to display a forming screen of the imaging information corresponding to a type of the certain radiation detector if it is determined by the determining unit that they are not equal,
   wherein the apparatus further comprises a forming unit configured to form the imaging information corresponding to the type of the registered radiation detector on the basis of a setting received through the forming screen, and
   wherein the associating unit is configured to associate the imaging information formed by the forming unit with the inherent information of the certain radiation detector.

4. The control apparatus according to claim 1,
   further comprising a forming unit configured to form the imaging information which is associated with the certain radiation detector on the basis of the selected imaging information,
   wherein the associating unit is configured to associate the imaging information formed by the forming unit with the inherent information of the certain radiation detector.

5. The control apparatus according to claim 4, wherein the forming unit is configured to form the imaging information which is associated with the inherent information of the certain radiation detector on the basis of whether or not the type information of the certain radiation detector is included in all of the imaging information selected through the selecting screen.

6. The control apparatus according to claim 1, wherein the imaging information is information in which at least either information regarding an imaging condition or information regarding an image processing condition is associated, as the information regarding the radiation imaging, with the type information of the radiation detector, and wherein the inherent information is a serial number of the radiation detector.

7. A control apparatus comprising:
a processor coupled to a memory and programmed to function as:
a specifying unit configured to specify, when a certain radiation detector is registered, type information of the certain radiation detector;
a determining unit configured to determine whether or not imaging information including the type information specified by the specifying unit has been formed as imaging information in which information regarding a radiation imaging is associated with the type information of the certain radiation detector;
a detecting unit configured to detect the imaging information including the specified type information if it is determined by the determining unit that the imaging information has been formed; and
an associating unit configured to associate the imaging information detected by the detecting unit with inherent information of the certain radiation detector, the inherent information being information capable of identifying the certain radiation detector.

8. The control apparatus according to claim 7, further comprising:
a display control unit configured to cause a display unit to display a forming screen of imaging information including the specified type information if it is determined by the determining unit that the imaging information is not formed; and
a forming unit configured to form the imaging information including the specified type information on the basis of a setting received through the forming screen,
wherein the associating unit is configured to associate the imaging information formed by the forming unit with the inherent information of the certain radiation detector.

9. The control apparatus according to claim 8, wherein if it is determined by the determining unit that the imaging information is not formed and if a forming rule of the imaging information has been predetermined, the forming unit is configured to form the imaging information including the specified type information on the basis of the forming rule.

10. The control apparatus according to claim 8, wherein the display control unit is configured to cause the display unit to display a recording information screen for presenting recording information in the case where the recording information including type information of an unavailable radiation detector and the associated imaging information was stored in a storage area of the control apparatus and in the case where the type information of the radiation detector and the specified type information are equal, and
wherein the detecting unit is configured to detect the imaging information included in the recording information in response to an instruction received through the recording information screen displayed by the display unit.

11. The control apparatus according to claim 7, wherein if an associating rule in the association has been predetermined, the associating unit is configured to associate the detected imaging information with the inherent information of the certain radiation detector on the basis of the associating rule.

12. The control apparatus according to claim 7, wherein if substitute apparatus information is not stored in a storage area of the certain radiation detector, the specifying unit is configured to specify the type information of the certain radiation detector, and if the substitute apparatus information has been stored in the storage area, the specifying unit is configured to specify a substitution-target radiation detector on the basis of the substitute apparatus information, and
wherein if the substitution-target radiation detector has been specified by the specifying unit, the detecting unit is configured to detect imaging information associated with the specified radiation detector.

13. The control apparatus according to claim 7, wherein the imaging information is information in which at least either information regarding an imaging condition or information regarding an image processing condition is associated, as the information regarding the radiation imaging, with the type information of the certain radiation detector, and
wherein the inherent information is a serial number of the radiation detector.

14. A control method which is executed by a control apparatus, comprising the steps of:
causing a display unit to display a selecting screen for presenting a list of imaging information of registered radiation detectors and receiving a selection from the list, the imaging information being information in which information regarding a radiation imaging is associated with type information of each radiation detector; and
associating in such a manner that when a certain radiation detector is registered, the imaging information selected through the displayed selecting screen is associated with inherent information of the certain radiation detector, the inherent information being information capable of identifying the certain radiation detector.

15. A control method which is executed by a control apparatus, comprising:
specifying, when a certain radiation detector is registered, type information of the certain radiation detector;
determining whether or not imaging information including the type information specified by the specifying step has been formed as imaging information in which information regarding a radiation imaging is associated with the type information of a radiation detector;
detecting the imaging information including the specified type information if it is determined by the determining step that the imaging information has been formed; and
associating the imaging information detected by the detecting step with inherent information of the certain radiation detector, the inherent information being information capable of identifying the certain radiation detector.

16. A non-transitory computer-readable storage medium storing a program for causing a computer to execute a method comprising:
causing a display unit to display a selecting screen for presenting a list of imaging information of registered radiation detectors and receiving a selection from the list, the imaging information being information in which information regarding a radiation imaging is associated with type information of each radiation detector; and
associating in such a manner that when a certain radiation detector is registered, the imaging information selected through the displayed selecting screen is associated with inherent information of the certain radiation detector, the inherent information being information capable of identifying the certain radiation detector.

17. A non-transitory computer-readable storage medium storing a program for causing a computer to execute a method comprising:
- specifying, when a certain radiation detector is registered, type information of the certain radiation detector;
- determining whether or not imaging information including the type information specified by the specifying step has been formed as imaging information in which information regarding a radiation imaging is associated with the type information of a radiation detector;
- detecting the imaging information including the specified type information if it is determined by the determining step that the imaging information has been formed; and
- associating the imaging information detected by the detecting step with inherent information of the certain radiation detector, the inherent information being information capable of identifying the certain radiation detector.

18. A control apparatus comprising:
- a display control unit configured to cause a display unit to display a selecting screen for presenting a list of imaging information of registered radiation detectors and receiving a selection from the list, the imaging information being information in which information regarding a radiation imaging is associated with type information of each radiation detector; and
- an associating unit configured to associate in such a manner that when a certain radiation detector is registered, the imaging information selected through the selecting screen is associated with inherent information of the certain radiation detector, the inherent information being information capable of identifying the certain radiation detector.

* * * * *